United States Patent [19]

Ahrens et al.

[11] Patent Number: 5,674,754
[45] Date of Patent: Oct. 7, 1997

[54] DIAGNOSTIC ASSAY FOR LATENT MATRIX METALLO-PROTEINASE NO. 9 AND USE THEREOF IN THE DIAGNOSIS OF RHEUMATOID AND INFLAMMATORY ARTHRITIS AND INFLAMMATORY BOWEL DISEASE

[75] Inventors: Diane Ahrens, Beacon Falls; Michael J. Niedbala, Oxford, both of Conn.

[73] Assignee: Bayer Corporation, Tarrytown, N.Y.

[21] Appl. No.: 424,315

[22] PCT Filed: Oct. 28, 1993

[86] PCT No.: PCT/US93/10382

§ 371 Date: Apr. 27, 1995

§ 102(e) Date: Apr. 27, 1995

[87] PCT Pub. No.: WO94/10208

PCT Pub. Date: May 11, 1994

Related U.S. Application Data

[63] Continuation-in-part of Ser. No. 968,554, Oct. 29, 1992, abandoned.

[51] Int. Cl.[6] ................................................ G01N 33/543
[52] U.S. Cl. .................... 436/518; 435/7.23; 435/320; 435/7.1; 424/94.67; 424/185.1; 530/326; 536/326; 536/27; 560/85
[58] Field of Search ............................ 435/7.23, 320, 435/7.1; 424/185.1, 94.67; 560/85; 536/27; 530/326; 436/518

[56] References Cited

U.S. PATENT DOCUMENTS

| | | | |
|---|---|---|---|
| 4,628,027 | 12/1986 | Gay | 435/7.23 |
| 4,923,818 | 5/1990 | Goldberg et al. | 435/320 |
| 4,992,537 | 2/1991 | Goldberg et al. | 536/27 |
| 5,260,059 | 11/1993 | Acott et al. | 424/94.67 |
| 5,270,447 | 12/1993 | Liotta et al. | 530/326 |
| 5,324,634 | 6/1994 | Zucker | 435/7.23 |
| 5,330,894 | 7/1994 | Ohmoto et al. | 435/7.4 |
| 5,372,809 | 12/1994 | Liotta et al. | 424/185.1 |
| 5,387,504 | 2/1995 | Mumford et al. | 435/7.1 |
| 5,403,952 | 4/1995 | Hagmann et al. | 560/85 |

FOREIGN PATENT DOCUMENTS

| | | |
|---|---|---|
| 5034353 | 2/1993 | Japan . |
| 9409825 | 5/1994 | WIPO . |

OTHER PUBLICATIONS

Dictionary of Biochemistry and Molecular Biology, 2nd Edition, J. Stenesh, Editor, John Wiley & Sons, New York, 1989, p. 382.

Clark, IM et al, Matrix, vol. 12(6), Dec. 1992, pp. 475–480.

Weiss, SJ et al; Biochem Pharmacolo, vol. 35(19), 1986, pp. 3189–3197.

Toubert, A; Arthritis and Rheum, vol. 28, pp. 958, 1985.

Docherty et al, Annals of Rheu Disease, 1990, vol. 49, pp. 469–479.

Bergmann, U. et al, J. Clin. Chem Clin. Biochem, vol. 27, 1989, pp. 351–359.

Cush, JJ et al, Arthritis Rheum, Jan. 1990, 33(1) pp. 19–28.

Mielants, H. et al, J Rheum, Jan. 1990, vol. 17(1), pp. 7–10.

Ramos–DeSimone, N. et al, Hybridoma, vol. 12, No. 4, 1993, pp. 349–363.

Meikle, M.C. et al; J Cell Science, 103, pp. 1093–1099, (1992).

Campbell, EJ et al; J Biolo Chem, vol. 262, No. 33, Nov. 25, 1987 pp. 15862–15868.

(List continued on next page.)

Primary Examiner—James C. Housel
Assistant Examiner—Ginny Allen Portner
Attorney, Agent, or Firm—Sprung Horn Kramer & Woods

[57] ABSTRACT

Elevated plasma levels of proMMP-9 and proMMP-9/TIMP-1 complex have been shown to correlate with and are useful in aiding the diagnosis of rheumatoid arthritis and inflammatory bowel disease; a hybridoma which produces a monoclonal antibody which specifically binds to and recognizes proMMP-9 and proMMP-9/TIMP-1 complex is disclosed and is designated mAb 277.13.

22 Claims, 6 Drawing Sheets

PATIENT GROUP

OTHER PUBLICATIONS

Hayakawa, T. et al; FEBS, vol. 298(1) pp. 29–32, Feb. 1992.

Birkedal–Hansen, B. et al; Biochem. 1988, vol. 27, pp. 6751–6758.

Hauschield, S. et al; Advances in Exper. Med. Biol, 1993, pp. 245–252, vol. 336.

Ogata, Y et al, J Biol. Chem, vol. 267(6), pp. 3581–3584 Feb. 1992.

Matache, C. et al, Roum. Arch. Microbiol Immunol, 51(4), Oct.–Dec. 1992, pp. 197–203.

Martisian, L. M., Trends in Genetics, vol. 6, pp. 121–125, 1990.

Murphy, G. et al, J. Cell Sci, vol. 92, pp. 487–495, 1989.

Kleinman, H K et al; Biochem; 1986, vol. 25, pp. 312–318.

Van Wart, H E et al, Pro. Natl. Acad Sci (USA), vol. 87, pp. 5578–5582, Jul. 1990.

Woessner, J.F., Jr; FASEB J, vol. 5, pp. 2145–2154, 1991.

Corcoran, ML et al, J Biol Chem., Jan. 5, 1992, vol. 267(1), pp. 515–519.

Moutsiakis, D et al, Conn. Tiss. Res., 1992, vol. 28, pp. 213–230.

Obata, K. et al, Clin. Chem. ACTA, Oct. 15, 1992, vol. 211(1-2) pp. 59–72.

Kodama, S et al, J. Immunol. Methods, Feb. 20, 1990, vol. 127(1), pp. 103–108.

DIAGNOSTIC ASSAY FOR LATENT MATRIX METALLO-PROTEINASE NO. 9 AND USE THEREOF IN THE DIAGNOSIS OF RHEUMATOID AND INFLAMMATORY ARTHRITIS AND INFLAMMATORY BOWEL DISEASE

This application is a continuation-in-part of U.S. patent application Ser. No. 07/968,554, which was filed on Oct. 29, 1992 now abandoned.

BACKGROUND OF THE INVENTION

1. Field of the Invention

The present invention relates to assay methods for detecting levels of specific enzymes in biological samples. More particularly, the present invention relates to methods for the detection of Matrix Metallo-Proteinase No. 9 (hereinafter "MMP" when referring to the class of matrix metalloproteinases and "MMP-9" when referring to matrix metalloproteinase No. 9 in particular). The inventive assay method is useful to diagnose rheumatoid arthritis, inflammatory arthritis (including psoriatic, gout, systemic lupus erythematous, and spondyl arthritis) and inflammatory bowel disease (hereinafter "IBD").

2. Description of the Related Art

MMPs are zinc-dependent endopeptidases that function in the physiological degradation of matrix connective tissue such as collagens, gelatin, fibronectin, elastin, laminin and proteoglycan (Woessner, 1991, *FASEB J.*, 5: 2145). MMP-9 is a 92 kDa proteinase which specifically degrades type IV, V, X, and XI collagen, and is sometimes referred to in the art as "96 kDa gelatinase" (Overall et al., 1991, *Infect. Immun.*, 59: 4687).

MMP-9 plays a role in leukocyte extravasation, a process involving a multiplicity of cell-to-cell and cell-to-matrix interactions during acute and chronic inflammatory reactions. An early response that triggers the inflammatory cascade is the recruitment and subsequent activation of polymorphonuclear leukocytes (hereinafter "PMN"). For PMNs to reach their targets, the basement membrane and connective tissue collagen must be hydrolyzed. This hydrolysis is carried out in part by MMP-9.

Physiological variances in MMP levels are known. For instance, significant increases in plasma 72 kDa gelatinase (MMP-2 levels have been observed in women during the second half of pregnancy as compared to early pregnancy and nonpregnant women (Zucker et al., 1992, *J. Immunol. Methods*, 148: 189).

Pathologically, MMPs have been identified as associated with several disease states. For example, anomalous MMP-2 levels have been detected in lung cancer patients, where it was observed that serum MMP-2 levels were significantly elevated in stage IV disease and in those patients with distant metastases as compared to normal sera values (Garbisa et al., 1992, *Cancer Res.*, 53: 4548). Also, using an ELISA methodology, it was observed that plasma levels of MMP-9 were elevated in patients with colon and breast cancer (Zucker et al., 1993, *Cancer Res.* 53: 140). However, these researchers did not investigate potential relationships among MMP-9 plasma levels in arthritis and IBD.

Elevated levels of stromelysin (MMP-3) and interstitial collagenase (MMP-1) have been noted in synovial fluid derived from rheumatoid arthritis (hereinafter "RA") patients as compared to post-traumatic knee injury (Walakovits et al., 1992, *Arth. Rheum.*, 35: 35). Hirose et al., 1992, *J. Rheumat.*, 19: 593, demonstrated the presence of 92–96 kDa MMP-9 activity and antigen in the synovial fluid of patients with inflammatory arthritis, including RA. However, these researchers did not investigate potential relationships among MMP-9 plasma levels in arthritis and IBD.

Increased levels of mRNA expression for collagenase type I (MMP-1) and collagenase type IV (MMP-2) have been shown to be increased in ulcerative colitis as compared to Crohn's disease and controls (Matthes et al., 1992, *Gastroenterology*, Abstract 661). However, plasma levels of these enzymes were not determined. Anthony et al., 1992, *Gastroenterology*, Abstract 591, demonstrated increased immuno-histochemical expression of the gelatinase antigen in a rabbit model of chronic inflammatory colitis. However, human material was not analyzed in this study. Bailey et al., 1990, *Biochem. Soc. Trans.*, 18: 896, demonstrated increased immuno-histochemical expression of the gelatinase antigen in the intestine of patients suffering from Crohn's disease as compared to normal intestines. However, plasma levels of this enzyme were not determined. Horowitz et al., 1987, *Clin. Biochem.*, 20: 79, demonstrated increased interstitial collagenase activity (MMP-1) in colonic mucosa of patients suffering IBD as compared with normal colonic mucosa. Plasma levels of MMP-9 were not determined.

None of these investigators report any relationships between MMP-9 levels in plasma samples and either arthritis IA or IBD.

Bergmann et al., 1989, *J. Clin. Chem. Clin. Biochem.*, vol. 27, pp. 351–359, report on the detection of leucocyte gelatinase MMP-9 in the synovial fluid of rheumatoid arthritis patients. However, plasma MMP-9 levels in arthritis or IBD patients were not measured.

Published Japanese Patent Document 5034353 purports to relate to monoclonal antibodies to human 92 kDa gelatinase.

SUMMARY OF THE INVENTION

We have identified antibodies which selectively recognize pro-MMP-9 and complexes of pro-MMP-9 with tissue inhibitor of matrix metallo proteinase-1 (TIMP-1), with no substantial binding to active MMP-9. Herein "pro-MMP-9", when referring to the present invention, unless otherwise indicated, shall be understood to refer to pro-MMP-9 and pro-MMP-9/TIMP-1 complexes, collectively. One of these antibodies, which has been designated mAb 277.13 (produced by a hybridoma cell line that has been deposited with the American Type Culture Collection (ATCC), Rockville, Md., USA) and is described in more detail below, reacts with high affinity to soluble latent forms of human MMP-9. This antibody has been used as a part of an immunologic detection assay which determines pro-MMP-9 levels in human biological fluids.

Our data indicate that the inventive antibodies are unique, as is the assay, which is capable of giving a quantitative measure of pro-MMP-9 levels in human biological fluids. Our data further indicate that pro-MMP-9 levels are a useful marker for providing information relevant to: (1) prognosis, (2) treatment decisions, and (3) as an indicator of treatment efficiency in rheumatoid arthritis and other chronic inflammatory diseases and IBD.

Thus, one embodiment of the present invention relates to a method for aiding in the diagnosis of rheumatoid and inflammatory arthritis in a patient, comprising the steps of determining the amount of pro-MMP-9 in a plasma sample obtained from said patient and comparing said measured amount of pro-MMP-9 to the mean amount of pro-MMP-9 in the normal population, whereby the presence of a significantly elevated amount of pro-MMP-9 in the patient's plasma is an indication of a rheumatoid or inflammatory arthritis condition.

A second embodiment of the present invention relates to a method for monitoring the progression of rheumatoid or inflammatory arthritis in a patient, comprising the steps of establishing a baseline value for plasma pro-MMP-9 in said patient, thereafter measuring the amount of pro-MMP-9 in a plasma sample obtained from said patient and comparing said measured amount of pro-MMP-9 to said baseline value, whereby a significantly elevated level of pro-MMP-9 indicates a deteriorating condition while a significantly reduced level indicates an improving condition.

A third embodiment of the present invention relates to a method for aiding in the diagnosis of inflammatory bowel disease in a patient, comprising the steps of determining the amount of pro-MMP-9 in a plasma sample obtained from said patient and comparing said measured amount of pro-MMP-9 to the mean amount of pro-MMP-9 in the normal population, whereby the presence of a significantly elevated amount of pro-MMPT-9 in the patient's plasma is an indication of an inflammatory bowel disease condition.

A fourth embodiment of the present invention relates to a method for monitoring the progression of inflammatory bowel disease in a patient, comprising the steps of establishing a baseline value for plasma pro-MMP-9 in said patient, thereafter measuring the amount of pro-MMP-9 in a plasma sample obtained from said patient and comparing said measured amount of pro-MMP-9 to said baseline value, whereby a significantly elevated level of pro-MMP-9 indicates a deteriorating condition while a significantly reduced level indicates an improving condition.

Typically, in respect to all of the above methods, the amount of pro-MMP-9 in the patient's plasma is measured by immunoassay, with an immunoassay that employs a monoclonal antibody being particularly preferred. Particularly useful as such monoclonal antibody are those which bind to the same epitope as mAb 277.13.

BRIEF DESCRIPTION OF THE DRAWINGS

The invention will now be further described with reference to the drawings, wherein.

DETAILED DESCRIPTION OF THE INVENTION

Figure 1:
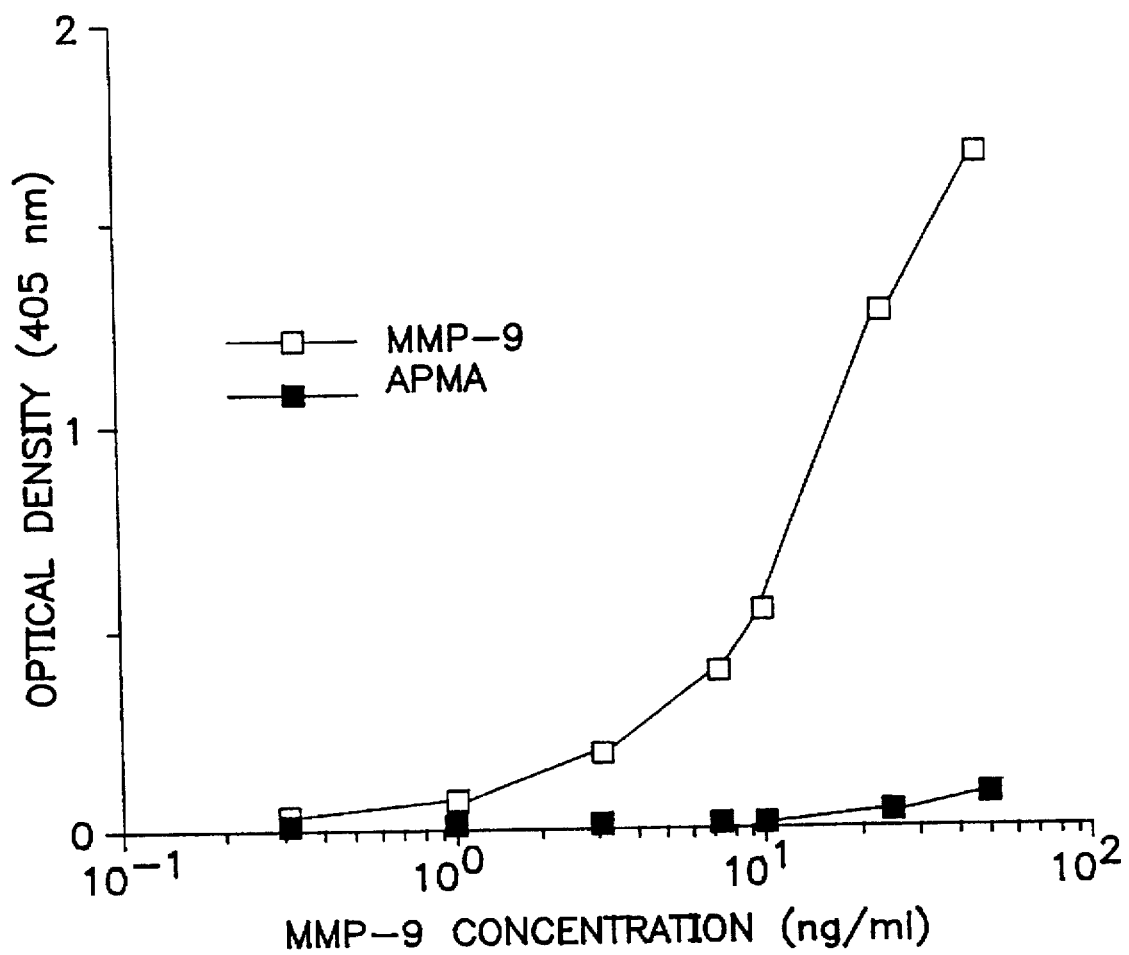
FIG. 1 is a graph depicting the light absorbance at various sample concentrations of pro-MMP-9 versus APMA-activated active enzyme using the present assay.

The measurement of pro-MMP-9 (which term, as used herein and as stated hereinbefore, includes complexes of pro-MMP-9 and TIMP-1) can be accomplished by any means appropriate. Typically, however, such measurement will be accomplished by immunoassay, that is, by determining the binding of an anti-(pro-MMP-9) antibody to pro-MMP-9 in the plasma under assay. As is well-known in the art, the determination of such antibody binding can be performed using a great variety of immunoassay formats.

The present invention is not limited to any particular immunoassay format. Preferred, however, will be heterogeneous immunoassay formats such as sandwich immunoassay formats in which the antigen of interest is detected by formation of a "sandwich" complex of a separation antibody and a detection antibody. The separation antibody is immobilized or immobilizable such as to a solid support, e.g., the walls of a microtiter plate, a latex particle, a macrobead, and the like. The detection antibody is labeled or labelable, directly or indirectly, with a detectable label such as, without limitation, enzymes or enzyme cofactors or substrates, chemiluminescent or fluorescent molecules, radioisotopes, and the like. The manner of detection can be any means conventionally associated with the particular label employed, e.g., a spectrophotometer in the case of enzymes or enzyme cofactors or substrates, a luminometer or fluorometer in the case of chemiluminescent or fluorescent molecules, or beta or gamma counters in the case of radioisotopes. Alternatively, the detection antibody can be detected by means of a labeled isotypic antibody.

The invention will now be further described with reference to the following non-limiting examples:

EXAMPLE 1

Preparation of pro-MMP-9 Antibodies

Preparation of pro-MMP-9: Pro-MMP-9 was isolated modifying the previously described procedures of Hibbs et al. (*J. Biol. Chem.*, 260: 2493–2500, 1984) and Wilhelm et al. (*J. Biol. Chem.*, 264: 17213–17221, 1989). Briefly, neutrophil preparations were isolated from 3 or more units of freshly drawn whole blood obtained from the New York Blood Center, Inc. (New York, N.Y.). Cells were resuspended in phosphate buffered saline (PBS) containing 100 ng/ml phorbol myristate acetate (PMA) in the presence of 50 mM diisopropylfluorophosphate (DFP), 1 μg/ml leupeptin and aprotinin, and 1 mg/ml catalase for 1 hr at 37° C. Supernatants were collected by centrifugation (300×g) and the samples were frozen at −70° C. All chromatographic methods were performed at 4° C. Thawed samples were concentrated 5-fold using an Amicon chamber equipped with a YM-10 membrane. The concentrate was pressure dialyzed against 0.02 M Tris-HCl, 0.1 M NaCl, 1 mM $CaCl_2$, 1 μM $ZnCl_2$, 0.001% Brij-35, 0.02% sodium azide ($NaN_3$), pH 7.5 and applied to DEAE ion exchange chromatography resin which was previously equilibrated with the same buffer at a flow rate of 0.4 ml/min. The column was extensively washed with the same buffer and gelatinase was eluted as 4 ml fractions from the column with 0.02 M Tris-HCl, 0.5 M NaCl, 1 mM $CaCl_2$, 1 μM $ZnCl_2$, 0.001% Brij-35, 0.02% $NaN_3$, pH 7.5. Gelatinase containing fractions were observed by gelatin zymography, loaded onto a gelatin agarose affinity resin and washed with the same buffer. Gelatinase activity was eluted at a flow rate of 1 ml/min from the column as 1 ml fractions with 0.02 M Tris-HCl, 1 M NaCl, 1 mM $CaCl_2$, 1 μM $ZnCl_{2,\ 0.001}$% Brij-35, 0.02% $NaN_3$, pH 7.5 containing 10% dimethyl sulfoxide (DMSO). The fractions containing gelatinase activity were pooled and dialyzed against 0.005 M Tris-HCl, 5 M NaCl, 0.5 mM $CaCl_2$, 0.1 μM $ZnCl_2$, 0.001% Brij-35, pH 7.4. The protein content associated with material was determined with a micro-BCA assay (Pierce, Rockford, Ill.), lyophilized and reconstituted to a desired working concentration (100 µg/ml).

The preparation of pro-MMP-9 specific polyclonal antibodies:

Purified latent form of human neutrophil MMP-9 (50 µg/animal) was emulsified with an equal volume of complete Freund's adjuvant. This mixture was administered to New Zealand White rabbits at multiple intradermal sites (30–50 sites) with 0.05 ml/site. Secondary immunizations were carried out on days 14, 21, 42 and 63 using MMP-9 (50 µg/animal) emulsified with an equal volume of incomplete Freund's adjuvant. Bleeds were taken at day 0, 28, 49 and 70 to determine antibody response.

The preparation of pro-MMP-9 specific monoclonal antibody (mAb 277.13):

Balb/c mice were immunized by intraperitoneal injection with purified latent form of human neutrophil MMP-9 (15 µg/animal) emulsified with an equal volume of complete Freund's adjuvant. Secondary immunizations were carried out on days 21 and 49 using MMP-9 (10 µg/animal) emulsified with an equal volume of incomplete Freund's adjuvant. After an additional seven days, the mice were immunized intravenously with 5 µg of immunogen and spleens were removed for fusion three days later.

Somatic cell hybrids were prepared by the method of Herzenberg and Milstein (*Handbook of Exp. Immunol.*, ed. Weir, D., Blackwell Scient. Public., 25.1–25.7, 1978) with some modifications (Lerner et al., 1980, *J. Exp. Med.*, 152: 1085–1101). The non-immunoglobulin secreting mouse myeloma cell line p3X63-Ag8.653 (Af8, ATCC No. CRL 1580) was cultured in RPMI 1640 medium containing 20% fetal bovine serum, 2 mM glutamine, 50 U/ml penicillin, and 50 µg/ml streptomycin. Single cell suspensions of spleen cells were prepared from immunized mice and mixed at a 2:1 ratio with Ag8 cells in serum-free RPMI 1640 medium. This cell mixture was fused by the dropwise addition of prewarmed 45% (w/v) polyethylene glycol-1450 (Eastman Kodak Co., Rochester, N.Y.) and subsequent dilution with 10 ml serum-free RPMI 1640 medium. After fusion, cells ($1\times10^6$ cells/well/ml) were seeded onto 24 well plates and hybrid cells were selected by hypoxanthine-aminopterin-thymidine supplemented culture medium. Hybridomas were screened for the desired antibody synthesis using enzyme linked immunosorbent assay (ELISA) and cell lines secreting antibodies of interest were cloned at least twice by limiting dilution using culture medium supplemented with 5 U/ml human recombinant IL-6 (Genzyme, Boston, Mass.).

Culture supernatants of hybridomas were screened for the presence of anti-pro-MMP-9 antibody using ELISA assays. Purified human neutrophil pro-MMP-9 (25 ng/well) was adsorbed to Immunolon I plates (Dynatech, Cambridge, Mass.) by overnight incubation at 4° C. in 50 µl 0.01 M sodium carbonate pH 9.5. Wells were blocked with PBS and bovine serum albumin (BSA), sequentially incubated with 100 µl of hybridoma supernatant, washed, and incubated with 100 µl of a 1:1000 dilution of peroxidase labeled affinity purified goat antimouse IgG (Kirkegaard and Perry Laboratories, Gaithersburg, Md.). Bound peroxidase was detected using tetramethylbenzidine according to the manufacturer's instruction (Kirkegaard and Perry Laboratories, Gaithersburg, Md.). Isotypes of positive hybrid supernatants were determined using an ELISA sandwich assay. Monoclonal antibodies were purified from ascites fluid using a protein A Sepharose column and the MAPs buffer system (Biorad Laboratories, Richmond, Calif.).

EXAMPLE 2

Pro-MMP-9 Immuno-Capture Sandwich Assay Development

Based upon ELISA and Western analysis, the antibodies-both polyclonal and monoclonal- recognized Pro-MMP-9 specifically, but not other MMPs or tissue inhibitor of matrix metalloproteinase (TIMP). By titrating human neutrophil pro-MMP-9 using various dilutions of primary and secondary antibody, optimal conditions for the MMP-9 immuno-capture sandwich ELISA were established.

96-well Immunolon I microtiter plates were coated with mAb 277.13 (1 µg/well) (Example 1) and incubated for 18 hrs at 4° C. in 0.01 M sodium carbonate pH 9.5. The plates were washed 5 times with 20 mM Tris HCl, 0.15 M NaCl, 0.05% Tween-20, pH 7.4 (washing buffer) and incubated for 1 hr at room temperature with 5% BSA in the same buffer to block nonspecific protein binding to assay wells.

The BSA was removed and the plates were washed with washing buffer and the standard human neutrophil pro-MMP-9 or patient samples were added for 2 hrs at room temperature. Samples were diluted in wash buffer containing 0.05% Tween-20 along with 1% BSA. The plates were washed with wash buffer (5 times) and incubated for 1 hr at room temperature with the rabbit polyclonal antisera (Example 1) at a 1:2000 dilution in wash buffer containing 1% BSA. This antisera was washed from the plates and the plates were then incubated with alkaline phosphatase-labeled mouse anti-rabbit mAb (Sigma Chemical Co., St. Louis, Mo.) for 1 hr at room temperature in wash buffer containing 1% BSA (dilution was 1:1000, mAb:1% BSA).

The plates were again washed 5 times and incubated with the substrate p-nitrophenyl phosphate (1 mg/ml) in 0.1 M glycine, 1 mM $MgCl_2$ and 1 µM $ZnCl_2$, pH 10.4. The absorbance at 405 nm was measured spectrophotometrically in an automated plate reader. The assay has a half maximal detection level of approximately 10 ng/ml with a log-linear range of detection of 0.3–100 ng/ml (FIG. 1).

FIG. 1 shows that the inventive assay detects pro-MMP-9 (MW of 92–96 kDa), but does not detect p-aminophenyl mercuric acetate (APMA) activated active MMP-9 (MW of 83 or 70 kDa). Data represent the mean values of triplicate determinations; S.D. was less than 10% of the mean.

Figure 2:
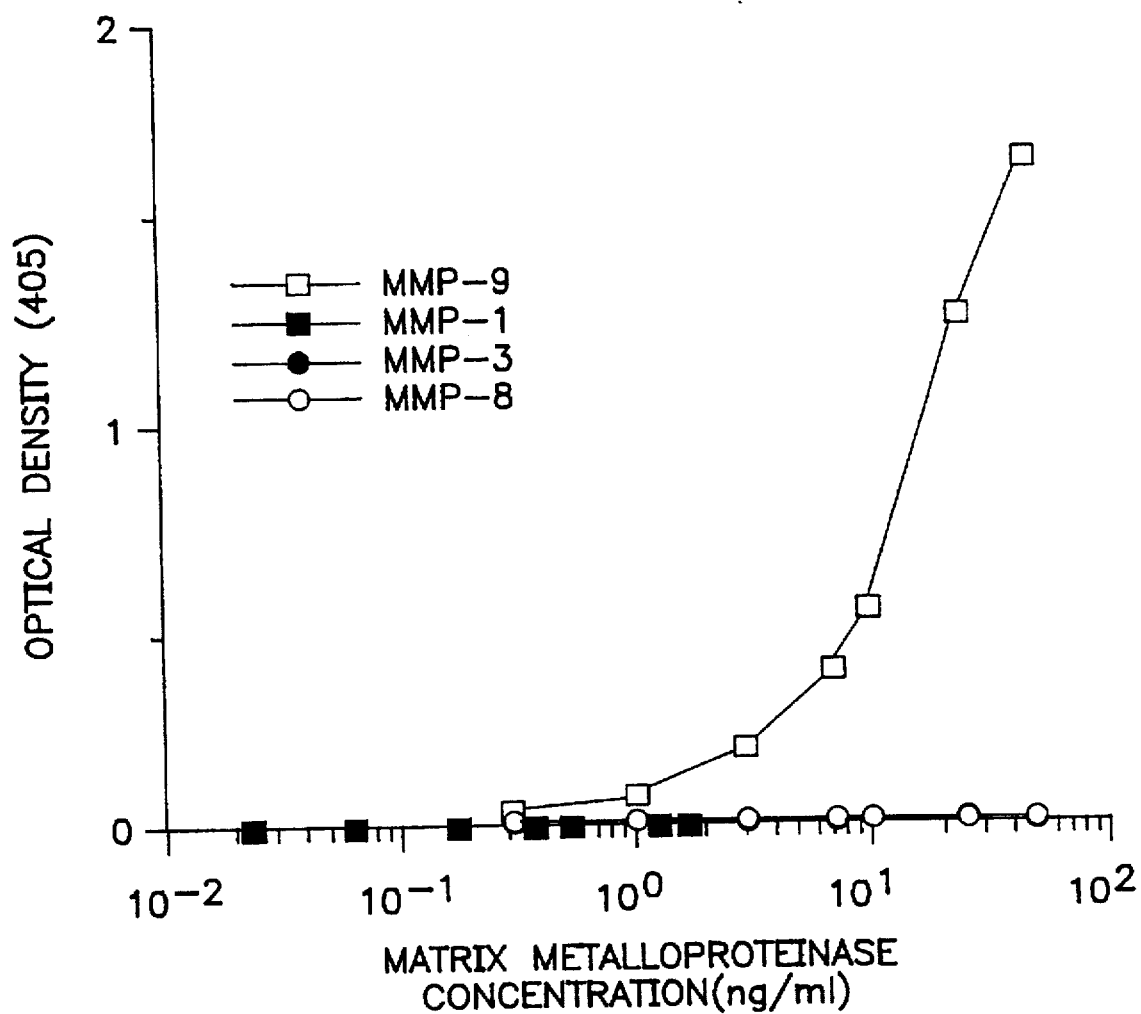
FIG. 2 is a graph depicting the light absorbance at various sample concentrations of various MMPs using the present assay.
Figure 3:
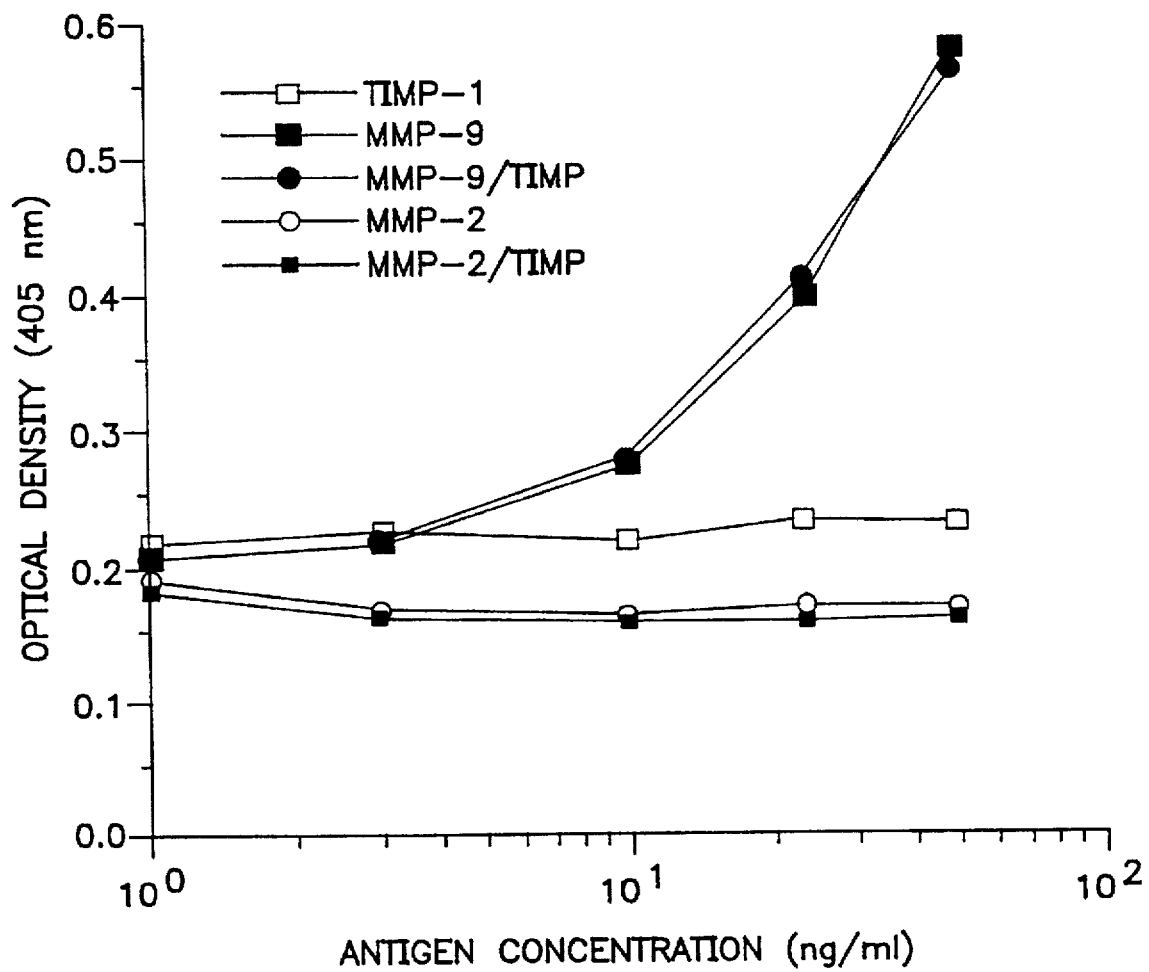
FIG. 3 is a graph depicting the light absorbance at various sample concentrations of TIMP-1, pro-MMP-9, pro-MMP-2 and enzyme/inhibitor complexes.

FIG. 2 shows that the inventive antibody is selective for pro-MMP-9 and fails to recognize human PMN collagenase (MMP-8), interstitial collagenase (MMP-1), and human stromelysin (MMP-3) at concentrations up to 50 ng/ml. The inventive assay also fails to recognize purified pro-MMP-2 and MMP-2/TIMP complexes. However, the inventive antibody will recognize pro-MMP-9/TIMP-1 complexes at a similar affinity as pro-MMP-9 alone (FIG. 3). Data represent the mean values of triplicate determinations; S.D. was less than 10% of the mean.

EXAMPLE 3

Analysis of pro-MMP-9 in Human Synovial Fluid of Arthritis Patients

Figure 4:
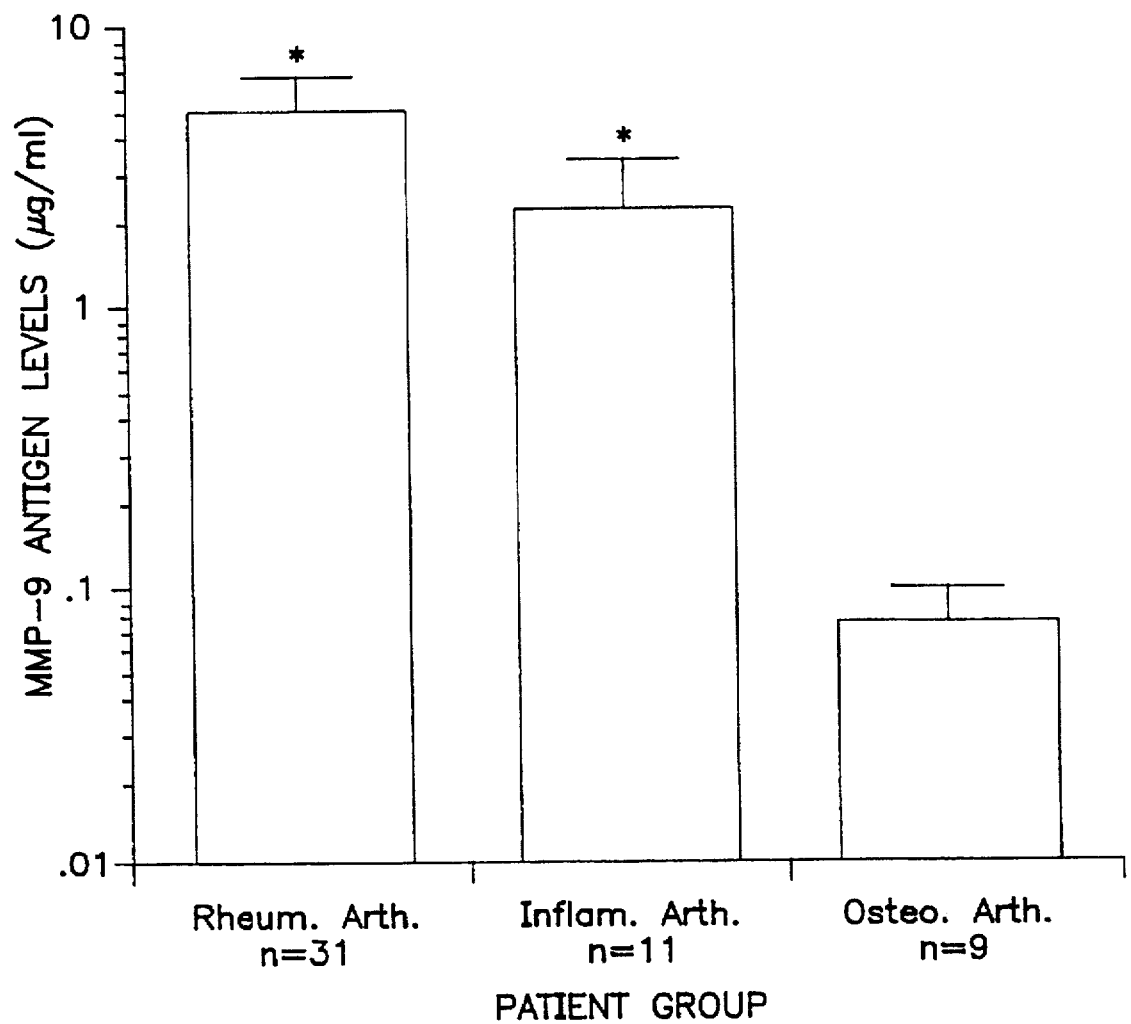
FIG. 4 is a graph depicting a comparison of the pro-MMP-9 antigen levels in synovial fluid samples from patients suffering from rheumatoid arthritis or inflammatory arthritis, and non-inflammatory osteoarthritis.

Human synovial fluid derived from patients with rheumatoid arthritis (n=31), patients with osteoarthritis (n=9), inflammatory arthritis patients which included IBD (n=3), gout (n=1), psoriatic arthritis (n=4), and spondylarthritis (n=3), were analyzed for pro-MMP-9 expression using the immuno-capture sandwich ELISA assay (Example 2). Detection in the linear range of the assay required a 1:50–1:1000 dilution of each respective sample. FIG. 4 shows the results of quantitation of latent MMP-9 in the synovial fluid from patients with osteoarthritis (OA), inflammatory arthritis (IA), and rheumatoid arthritis (RA). Synovial fluids from patients with RA and from patients with OA were diluted and analyzed using the immuno-capture ELISA assay. The mean values ± standard error of 0.07±0.02 Bg/ml for the OA group were observed as compared to RA samples which displayed latent MMP-9 levels of 6.7±2.6 Bg/ml and IA levels were 2.4±0.7 µg/ml. These differences were observed to be significant (Bonferroni modification of a two-tailed Studentjs t-Test for unpaired values). Asterisks denote significance P<0.05.

These data indicate that RA synovial fluids display over a 60-fold elevation in pro-MMP-9 levels, while synovial fluids derived from IA patients displayed a 34-fold elevation in pro-MMP-9 levels above OA pro-MMP-9 levels.

EXAMPLE 4

Determination of pro-MMP-9 in Human Plasma of Arthritis Patients

Human plasma derived from patients with rheumatoid arthritis (n=17), inflammatory arthritis (n=9) and from normal individuals (n=60) were analyzed for pro-MMP-9 expression using the immuno-capture sandwich ELISA assay (Example 2). Detection in the linear range of the assay required a 1:100–1:1000 dilution of each respective sample. Normal plasma (n=60) demonstrated pro-MMP-9 levels of 0.56±0.1 µg/ml as compared to RA samples (n=17) which displayed pro-MMP-9 levels of 3.5±0.8 µg/ml and IA pro-MMP-9 levels of 0.25±0.1 µg/ml. These differences were noted to be significant using a Bonferroni modification of a two-tailed student's t-test for unpaired values.

Figure 5:
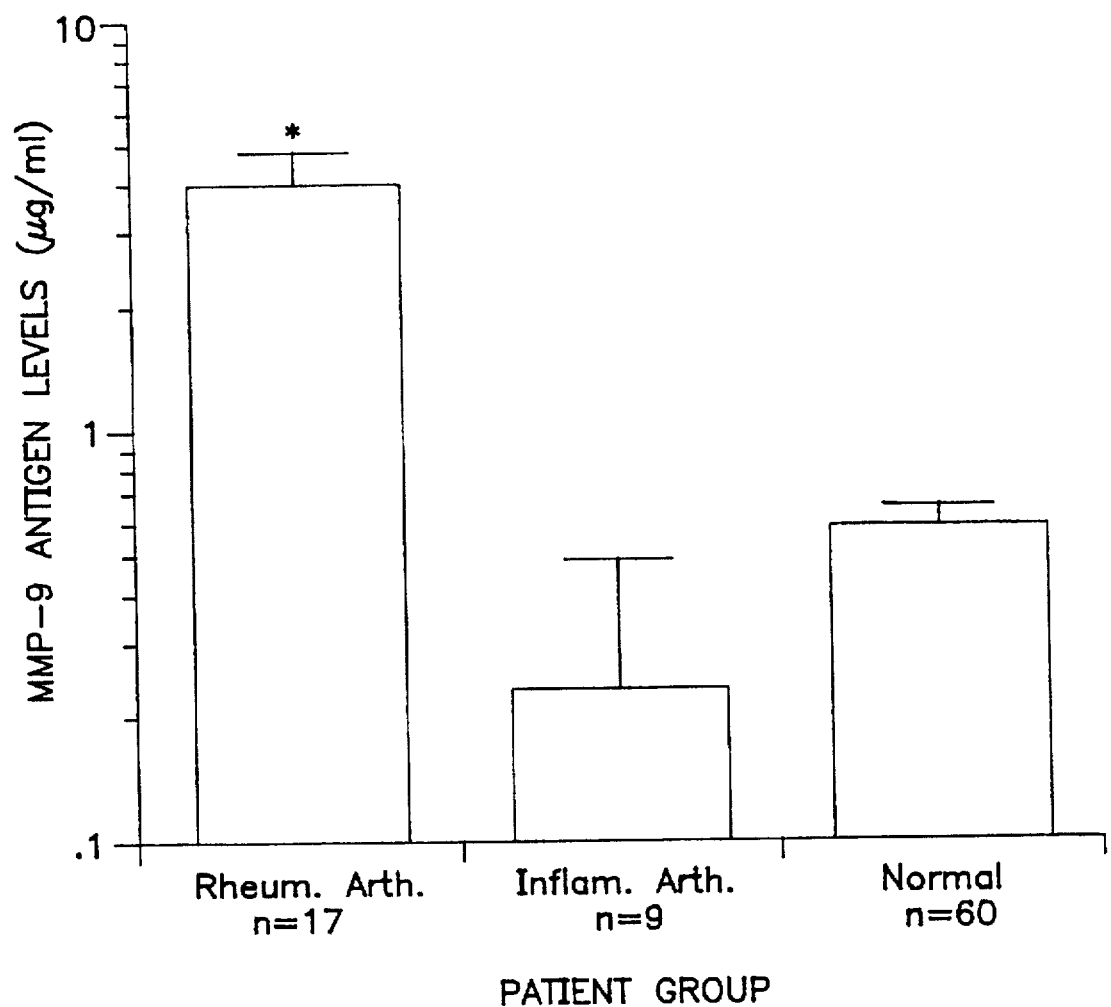
FIG. 5 is a graph depicting a comparison of the pro-MMP-9 antigen levels in plasma samples from patients suffering from rheumatoid arthritis or inflammatory arthritis, and normal controls.

These data indicate that RA plasma displays over a 6-fold elevation in latent MMP-9 levels as compared to normal plasma. FIG. 5 graphically depicts these results, showing the quantitation of latent MMP-9 in the plasma obtained from patients with RA, IA, and normal individuals. Bars depict the mean values ± standard error, as stated above. Asterisks denote significance P<0.05.

EXAMPLE 5

Figure 6:
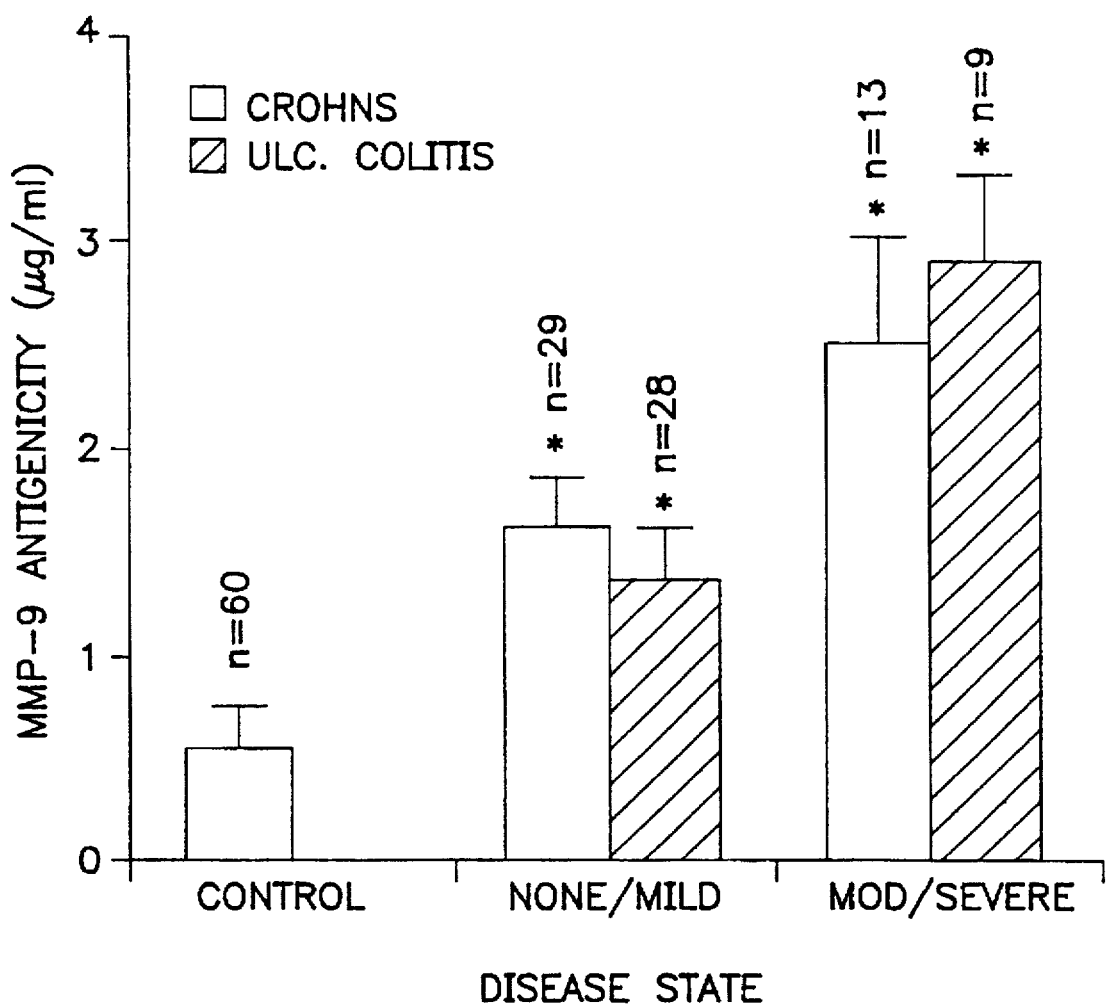
FIG. 6 is a graph depicting a comparison of the pro-MMP-9 antigen levels in plasma samples from patients suffering from ulcerative colitis or Crohnjs Disease, and normal controls.

Analysis of pro-MMP-9 in Human Plasma of Ulcerative Colitis and Crohn's Disease Patients Human plasma derived from ulcerative colitis and Crohn's disease patients was analyzed for pro-MMP-9 expression using the immuno-capture sandwich ELISA assay (Example 2). Pro-MMP-9 antigen detection in the linear range of the assay required a 1:50–1:1000 dilution of each respective plasma sample. Plasma derived from patients with moderate to severe ulcerative colitis (n=9) based on physical diagnosis, demonstrated latent MMP-9 levels of 2.9±0.4 µg/ml compared to normal control samples (n=60) which displayed latent MMP-9 levels of 0.56±0.1 µg/ml (FIG. 6). Plasma obtained from ulcerative colitis with no or mild disease had pro-MMP-9levels of 1.4±0.3 µg/ml. In addition, plasma obtained from patients with moderate to severe Crohn's disease (n=13) had latent MMP-9 levels of 2.5±0.5 µg/ml. Crohn's patients with no or mild disease (n=29) exhibited pro-MMP-9 levels of 1.6±0.3 µg/ml. These data indicate that both ulcerative colitis and Crohn's disease plasma samples derived from patients with moderate/severe disease activity display a significant 4- to 5-fold elevation in latent MMP-9 levels compared to control plasma samples. This increase in pro-MMP-9 was reduced in both cases to a 2- to 3-fold elevation in the no or mild disease activity group compared to control plasma samples displaying a correlation with clinical disease status.

In FIG. 6, the mean values ± standard error are shown for each respective group. Differences amongst the groups were analyzed using the Bonferroni modification of a two-tailed Student's t-Test for unpaired values. Asterisks denote significance P<0.05: * different from control.

It will be appreciated that the instant specification and claims are set forth by way of illustration and not limitation, and that various modifications and changes may be made without departing from the spirit and scope of the present invention. The claims are intended to cover such modification and changes either literally or pursuant to the doctrine of equivalents.

We claim:

1. A hybridoma, wherein the hybridoma produces a monoclonal antibody which specifically binds proMMP-9 and proMMP-9/TIMP-1 complex and the monoclonal antibody is designated mAB 277.13.

2. The monoclonal antibody mAb 277.13 which specifically binds proMMP-9 and proMMP-9/TIMP-1 complex.

3. A method for aiding in the diagnosis of rheumatoid arthritis in a patient, comprising the steps of determining the amount of pro-MMP-9 in a plasma sample obtained from said patient and comparing said determined amount of pro-MMP-9 to the mean amount of plasma pro-MMP-9 in the normal population, whereby the presence of an elevated amount of pro-MMP-9 in the patient's plasma is an indication of increased probability of rheumatoid arthritis.

4. The method of claim 4 wherein the amount of pro-MMP-9 in the patient's plasma is measured by immunoassay.

5. The method of claim 4 wherein the immunoassay employs a monoclonal antibody.

6. The method of claim 5 wherein said monoclonal antibody binds specifically to an epitope present in pro-MMP-9 and pro-MMP-9/TIMP-1 complexes.

7. The method of claim 6 wherein said monoclonal antibody mAb 277.13.

8. A method for monitoring the progression of rheumatoid arthritis in a patient, comprising the steps of establishing a baseline value for plasma pro-MMP-9 in said patient, thereafter measuring the amount of pro-MMP-9 in a plasma sample obtained from said patient and comparing said measured amount of plasma pro-MMP-9 to said baseline value, whereby an elevated level of plasma pro-MMP-9 indicates a deteriorating condition while a reduced level indicates an improving condition.

9. The method of claim 8 wherein the amount of pro-MMP-9 in the patient's plasma is measured by immunoassay.

10. The method of claim 9 wherein the immunoassay employs a monoclonal antibody.

11. The method of claim 10 wherein said monoclonal antibody binds specifically to an epitope present in pro-MMP-9 and pro-MMP-9/TIMP-1 complexes.

12. The method of claim 11 wherein said monoclonal antibody is mAb 277.13.

13. A method for aiding in the diagnosis of inflammatory bowel disease in a patient, comprising the steps of determining the amount of pro-MMP-9 in a plasma sample obtained from said patient and comparing said determined amount of plasma pro-MMP-9 to the mean amount of plasma pro-MMP-9 in the normal population, whereby the presence of an elevated amount of pro-MMP-9 in the patient's plasma is an indication of an inflammatory bowel disease condition.

14. The method of claim 13 wherein the amount of pro-MMP-9 in the patient's plasma is measured by immunoassay.

15. The method of claim 14 wherein the immunoassay employs a monoclonal antibody.

16. The method of claim 18 wherein said monoclonal antibody binds specifically to an epitope present in pro-MMP-9 and pro-MMP-9/TIMP-1 complexes.

17. The method of claim 16 wherein said monoclonal antibody is mAb 277.13.

18. A method for monitoring the progression of inflammatory bowel disease in a patient, comprising the steps of measuring a baseline value for plasma pro-MMP-9 in a plasma sample obtained from said patient and comparing said measured amount of pro-MMP-9 to said baseline value, whereby an elevated level of pro-MMP-9 indicates a deteriorating condition while a reduced level indicates an improving condition.

19. The method of claim 18 wherein the amount of pro-MMP-9 in the patient's plasma is measured by immunoassay.

20. The method of claim 19 wherein the immunoassay employs a monoclonal antibody.

21. The method of claim 20 wherein said monoclonal antibody binds specifically to an epitope present in pro-MMP-9 and pro-MMP-9/TIMP-1 complexes.

22. The method of claim 21 wherein said monoclonal antibody is mAb 277.13.

* * * * *

UNITED STATES PATENT AND TRADEMARK OFFICE
CERTIFICATE OF CORRECTION

PATENT NO. : 5,674,754
DATED : October 7, 1997
INVENTOR(S) : Ahrens, et al.

It is certified that error appears in the above-indentified patent and that said Letters Patent is hereby corrected as shown below:

Col. 8, line 27   Delete claim " 4 " and substitute -- 3 --

Col. 9, line 3    Delete claim " 18 " and substitute -- 15 --

Signed and Sealed this

Twelfth Day of October, 1999

Attest:

Q. TODD DICKINSON

Attesting Officer     Acting Commissioner of Patents and Trademarks